(12) United States Patent
Yan et al.

(10) Patent No.: US 12,207,926 B2
(45) Date of Patent: Jan. 28, 2025

(54) BLOOD COLLECTION DEVICES, SYSTEMS, AND METHODS

(71) Applicant: Becton, Dickinson and Company, Franklin Lakes, NJ (US)

(72) Inventors: Bo Yan, Shanghai (CN); Xiwei Chen, Shanghai (CN); Tao Jiang, Shanghai (CN); Olivia Hu, Shanghai (CN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/138,601

(22) Filed: Apr. 24, 2023

(65) Prior Publication Data

US 2023/0255530 A1  Aug. 17, 2023

Related U.S. Application Data

(62) Division of application No. 17/014,765, filed on Sep. 8, 2020, now Pat. No. 11,666,257.

(Continued)

(51) Int. Cl.
*A61B 5/00* (2006.01)
*A61B 5/15* (2006.01)

(52) U.S. Cl.
CPC .. *A61B 5/150992* (2013.01); *A61B 5/150351* (2013.01); *A61B 5/150946* (2013.01)

(58) Field of Classification Search
CPC ........ A61B 5/150992; A61B 5/150351; A61B 5/150946; A61B 5/15003;

(Continued)

(56) References Cited

U.S. PATENT DOCUMENTS

| | | |
|---|---|---|
| 4,588,160 A | 5/1986 | Flynn |
| 4,709,195 A | 11/1987 | Hellekson et al. |

(Continued)

FOREIGN PATENT DOCUMENTS

| | | |
|---|---|---|
| CA | 2975414 A1 | 8/2016 |
| CN | 201578681 U | 9/2010 |

(Continued)

OTHER PUBLICATIONS

Promepla, "Multi Step Clamp—Clamps / Clips—Promepla," Mar. 1, 2021, XP055780646, pp. 2-3 and 5-6, Retrieved from the Internet: <https://catalog.promepla.com/subcategory/multi-step-clamps>.

(Continued)

*Primary Examiner* — May A Abouelela
(74) *Attorney, Agent, or Firm* — Kirton McConkie; Whitney Blair; Kevin Stinger

(57) ABSTRACT

A vascular access system which may be configured for blood draw may include a housing, which may include a distal end, a proximal end, and a slot disposed between the distal end and the proximal end. The slot may include a notch. The vascular access system may include a cannula hub, which may be disposed within the housing and movable with respect to the slot. The cannula hub may include a tab extending through the slot. The vascular access system may include a cannula extending distally from the cannula hub. In response to the tab being disposed within the notch, a distal tip of the cannula may be disposed within the housing. In response to advancing the tab along the slot to a distal end of the slot, the distal tip of the cannula is disposed distal to the distal end of the housing.

4 Claims, 13 Drawing Sheets

Related U.S. Application Data

(60) Provisional application No. 62/898,428, filed on Sep. 10, 2019.

(58) Field of Classification Search
CPC ............ A61B 5/150221; A61B 5/153; A61M 25/0693; A61M 2005/1585; A61M 2039/0202; A61M 2039/062; A61M 25/0631; A61M 39/0606; A61M 39/284; A61M 25/0606; A61M 25/0097; A61M 5/1626; A61M 5/158; A61M 2005/1587; A61M 39/02
See application file for complete search history.

(56) References Cited

U.S. PATENT DOCUMENTS

| | | | |
|---|---|---|---|
| 5,352,205 | A | 10/1994 | Dales et al. |
| 6,592,558 | B2* | 7/2003 | Quah ................ A61M 39/284 128/912 |
| 6,644,618 | B1* | 11/2003 | Balbo ................ A61M 39/284 251/9 |
| 7,434,779 | B2* | 10/2008 | Werth .................... F16K 7/063 251/4 |
| 7,686,279 | B2* | 3/2010 | Nerbonne .......... A61M 39/284 604/250 |
| D637,712 | S* | 5/2011 | Chau .......................... D24/129 |
| 8,267,370 | B2* | 9/2012 | Fisher ................ A61M 39/288 251/7 |
| 8,328,457 | B2* | 12/2012 | Werth ................ A61M 39/1011 403/313 |
| 8,328,763 | B2* | 12/2012 | Traversaz ......... A61M 5/14244 604/250 |
| 8,617,119 | B2* | 12/2013 | Liversidge ............ A61M 5/326 604/110 |
| 9,352,099 | B2* | 5/2016 | Roberts ............... A61M 5/3272 |
| 9,498,596 | B1* | 11/2016 | Hakky .............. A61M 25/0905 |
| 9,585,784 | B2* | 3/2017 | Matthiassen ....... A61M 25/0111 |
| 9,763,395 | B1 | 9/2017 | Hinkle ...................... F17D 1/08 |
| 10,342,930 | B1* | 7/2019 | Infranger ............ A61M 5/3243 |
| 10,548,609 | B2* | 2/2020 | Ramsey ............... A61B 17/083 |
| D884,885 | S* | 5/2020 | Hu .............................. D24/128 |
| 11,052,201 | B2* | 7/2021 | Infranger ............. A61M 5/3271 |
| 11,083,841 | B2* | 8/2021 | Mathias ........... A61B 5/150534 |
| 11,234,626 | B2* | 2/2022 | Bullington ....... A61B 5/150267 |
| 11,419,531 | B2* | 8/2022 | Bullington ............ A61B 5/154 |
| 11,666,257 | B2* | 6/2023 | Yan ................... A61M 25/0631 600/583 |
| 2006/0282044 | A1 | 12/2006 | Mohammed |
| 2007/0233014 | A1* | 10/2007 | Yang ................. A61M 25/0631 604/198 |
| 2011/0307126 | A1 | 12/2011 | Hogerstrom |
| 2013/0066280 | A1 | 3/2013 | Wallin |
| 2013/0226344 | A1 | 8/2013 | Wong et al. |
| 2016/0009410 | A1 | 1/2016 | Derenick et al. |
| 2016/0354539 | A1 | 12/2016 | Tan et al. |
| 2017/0168146 | A1 | 6/2017 | Boehmke |
| 2019/0374749 | A1* | 12/2019 | Akcay ............... A61M 25/0606 |
| 2019/0381234 | A1* | 12/2019 | Shidham ................. A61M 1/14 |
| 2020/0008898 | A1* | 1/2020 | Rousche ........... A61M 5/16813 |
| 2020/0023166 | A1* | 1/2020 | Burkholz ........... A61M 25/0111 |
| 2020/0023176 | A1* | 1/2020 | Hu ........................ A61M 25/09 |
| 2020/0046946 | A1* | 2/2020 | Staley ............... A61M 25/0625 |
| 2020/0078579 | A1* | 3/2020 | Harding .......... A61M 25/09041 |
| 2020/0197667 | A1* | 6/2020 | Gupta ............... A61M 25/0618 |
| 2020/0230368 | A1* | 7/2020 | Breindel .......... A61M 25/0631 |
| 2020/0330015 | A1* | 10/2020 | Price ................ A61B 5/150389 |
| 2020/0376249 | A1* | 12/2020 | Lockhart ............ A61M 25/00 |
| 2021/0016066 | A1* | 1/2021 | Singh ................ A61M 25/0097 |
| 2021/0100985 | A1* | 4/2021 | Akcay ............... A61M 25/0606 |
| 2021/0106262 | A1* | 4/2021 | Lynn ................ A61M 25/0606 |
| 2021/0138162 | A1* | 5/2021 | Nakagami ........... A61M 5/158 |
| 2021/0138200 | A1* | 5/2021 | Chong ............. A61M 25/0014 |
| 2021/0177276 | A1* | 6/2021 | Arrizza ................ A61B 5/0215 |
| 2021/0219890 | A1* | 7/2021 | Ivosevic .......... A61B 5/150633 |
| 2021/0369159 | A1* | 12/2021 | Wilkinson .......... A61M 5/3275 |

FOREIGN PATENT DOCUMENTS

| | | |
|---|---|---|
| CN | 201591899 U | 9/2010 |
| CN | 104984428 A | 10/2015 |
| CN | 207356323 U | 5/2018 |
| EP | 0652020 A2 | 5/1995 |
| EP | 2044970 A1 | 4/2009 |
| JP | 2002532203 A | 10/2002 |
| JP | 2006051084 A | 2/2006 |
| WO | 0108740 A1 | 2/2001 |
| WO | 200147582 A1 | 7/2001 |
| WO | 2005087306 | 9/2005 |
| WO | 2006096633 A1 | 9/2006 |
| WO | 2016168737 A1 | 10/2016 |
| WO | 2017074684 A1 | 5/2017 |

OTHER PUBLICATIONS

Urocare, "Urocare 2018 Product Catalog," website, Dec. 31, 2018, Retrieved from the Internet: <https://www.urocare.com/EN/Documents/CAT2018-81010100B.pdf>.

Urocare, "Urocare Six-Position Adjustable Tube Clamp—6999," website, Mar. 11, 2014, XP055780629, Retrieved from the Internet: <https://www.vitalitymedical.com/urocare-adjustable-thumb-clamp.html>.

* cited by examiner

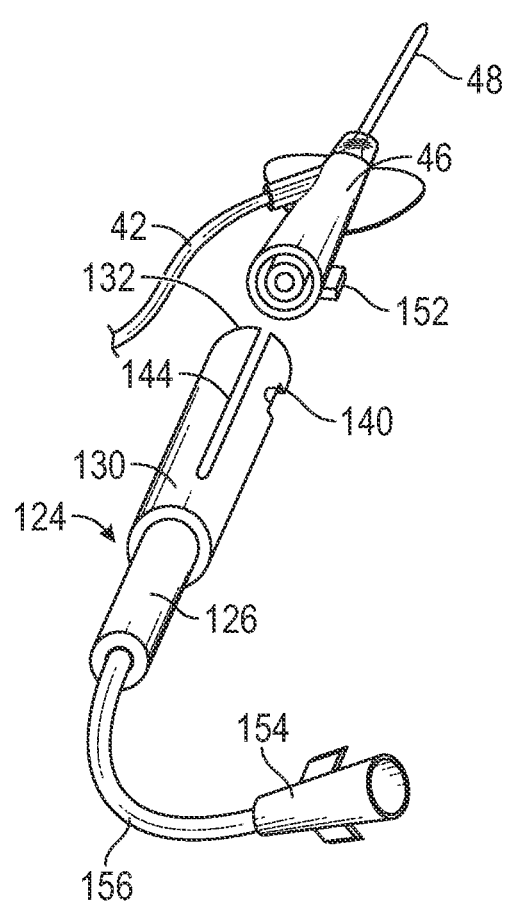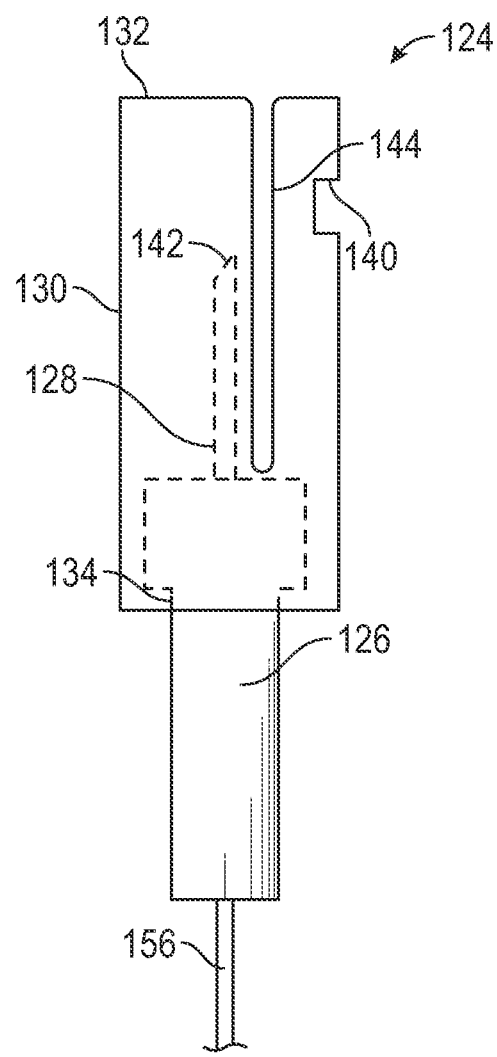
FIG. 5A
FIG. 5B

BLOOD COLLECTION DEVICES, SYSTEMS, AND METHODS

RELATED APPLICATIONS

This application is a divisional of U.S. patent application Ser. No. 17/014,765, filed Sep. 8, 2020, and entitled BLOOD COLLECTION DEVICES, SYSTEMS, AND METHODS, which claims the benefit of U.S. Provisional Application No. 62/898,428, filed Sep. 10, 2019, and entitled BLOOD COLLECTION DEVICES, SYSTEMS, AND METHODS which are incorporated herein in their entirety.

BACKGROUND

Intravenous catheters are commonly used for a variety of infusion therapies. For example, intravenous catheters may be used for infusing fluids, such as normal saline solution, various medicaments, and total parenteral nutrition, into a patient. Intravenous catheters may also be used for withdrawing blood from the patient.

Common types of intravenous catheter are peripheral IV catheters ("PIVCs"), peripherally inserted central catheters ("PICCs"), and midline catheters. Intravenous catheters may include "over-the needle" catheters, which may be mounted over a needle having a sharp distal tip. The sharp distal tip may be used to pierce skin and the vasculature of the patient. Insertion of the intravenous catheter into the vasculature may follow the piercing of the vasculature by the needle. The needle and the intravenous catheter are generally inserted at a shallow angle through the skin into the vasculature of the patient with a bevel of the needle facing up and away from the skin of the patient.

In order to verify proper placement of the introducer needle and/or the intravenous catheter in the vasculature, a user generally confirms that there is flashback of blood, which may be visible to the user. In some instances, the introducer needle may include a notch disposed towards a distal end of the introducer needle, and in response to the distal tip of the introducer needle being positioned within the vasculature, blood may flow proximally through a needle lumen, exit the needle lumen through the notch, and then travel proximally between an outer surface of the introducer needle and an inner surface of the intravenous catheter.

Accordingly, where the intravenous catheter is at least partially transparent, the user may visualize a small amount of blood "flashback" and thereby confirm placement of the intravenous catheter within the vasculature. Presence of a vasculature entrance indicator, such as flashback, may facilitate successful placement of intravenous catheters. Once placement of the introducer needle within the vasculature has been confirmed, the user may temporarily occlude flow in the vasculature and withdraw the introducer needle, leaving the intravenous catheter in place for future blood withdrawal and/or fluid infusion.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure generally relates to vascular access devices, systems, and methods. In some embodiments, a vascular access device may include a housing, which may include a distal end, a proximal end, and a lumen extending between the distal end and the proximal end. In some embodiments, the housing may include a slot disposed between the distal end and the proximal end. In some embodiments, the slot may include a notch.

In some embodiments, the vascular access device may include a cannula hub, which may be disposed within the housing and movable with respect to the slot. In some embodiments, the cannula hub may include a tab, which may extend through the slot. In some embodiments, a cannula may extend distally from the cannula hub. In some embodiments, the cannula may include a distal tip. In some embodiments, in response to the tab being disposed within the notch, the distal tip of the cannula may be disposed within the housing. In some embodiments, in response to advancing the tab along the slot to a distal end of the slot, the distal tip of the cannula may be disposed distal to the distal end of the housing.

In some embodiments, the vascular access system may include an extension tube coupled to a proximal end of the cannula hub and extending through the proximal end of the housing. In some embodiments, a blood collection device may be coupled to an adapter disposed at a proximal end of the extension tube. In some embodiments, the proximal end of the housing may include a cap.

In some embodiments, the vascular access system may include a catheter assembly, which may include a catheter adapter. In some embodiments, the catheter adapter may include a body disposed within the distal opening of the housing. In some embodiments, the body may include a distal end, a proximal end, a lumen extending through the distal end of the body and the proximal end of the body. In some embodiments, the proximal end of the body may be coupled to the distal end of the housing. In some embodiments, a catheter may extend from the distal end of the body of the catheter adapter and may be secured within the catheter adapter.

In some embodiments, the catheter adapter may include a side port. In some embodiments, the catheter assembly may include a pinch clamp device and an extension tube extending from the side port and through the pinch clamp device. In some embodiments, the pinch clamp device may include a first arm, which may include a first end and a second end. In some embodiments, the first end may include a first lip and a second lip. In some embodiments, the second end may include a first clamping surface.

In some embodiments, the pinch clamp device may include a second arm, which may include a first end and a second end. In some embodiments, the first end may include a terminal end. In some embodiments, the second end may include a second clamping surface positioned opposite the first clamping surface. In some embodiments, the pinch clamp device may include a hinge interconnecting the second end of the first arm and the second end of the second arm.

In some embodiments, the catheter assembly may include a wedge disposed within the lumen of the catheter adapter. In some embodiments, the wedge may be constructed of metal. In some embodiments, the wedge may secure the catheter within the catheter adapter. In some embodiments, in response to advancing the tab along the slot to a distal end of the slot, the distal tip of the cannula may be disposed within the wedge.

In some embodiments, in response to the terminal end being engaged with the first lip, the pinch clamp may be configured to partially occlude a portion of the tube disposed between the first clamping surface and the second clamping surface such that air passes the portion but blood does not. In some embodiments, in response to the terminal end being engaged with the second lip, the pinch clamp may be configured to occlude the portion of the tube disposed between the first clamping surface and the second clamping surface such that neither air nor blood pass the portion.

In some embodiments, a method, which may be used to collect blood from a patient, may include positioning the pinch clamp device at a proximal end of the extension tube of the vascular access system. In some embodiments, the vascular access system may include a catheter system. After positioning the pinch clamp device at the proximal end of the extension tube, the catheter may be inserted into vasculature of the patient. In some embodiments, after inserting the catheter into vasculature of the patient, the proximal end of the catheter adapter may be disinfected. In some embodiments, after disinfecting the proximal end of the catheter adapter, the housing may be coupled to the proximal end of the catheter adapter.

In some embodiments, after coupling the housing to the proximal end of the catheter adapter, the tab may be advanced along the slot to a distal end of the slot. In some embodiments, in response to advancing the tab along the slot to the distal end of the slot, the distal tip of the cannula may pass through a septum disposed within the lumen of the catheter adapter. In some embodiments, an outer surface of the body of the catheter adapter may include a protrusion. In some embodiments, an inner surface of the housing may include an L-shaped slot, which may extend from the distal end of the housing. In some embodiments, coupling the housing to the proximal end of the catheter adapter may include inserting the protrusion into the L-shaped slot and rotating the catheter adapter within the L-shaped slot.

In some embodiments, after the housing is coupled to the proximal end of the catheter adapter, blood may be drawn through the cannula. In some embodiments, after blood is drawn through the cannula and collected in the blood collection device, the tab may be moved along the slot from the distal end of the slot into the notch. In some embodiments, in response to moving the tab along the slot from the distal end of the slot into the notch, the distal tip of the cannula may be retracted into the housing. In some embodiments, after the cannula is retracted into the housing, the housing may be uncoupled from the proximal end of the catheter adapter.

In some embodiments, after the housing is uncoupled from the proximal end of the catheter adapter, the adapter may be flushed. In some embodiments, after the adapter is flushed, the terminal end may be disengaged from the first lip such that the pinch clamp device is in an open configuration. In some embodiments, when the pinch clamp device is in the open configuration, the catheter may be flushed via the extension tube. In some embodiments, after the catheter is flushed, a vent plug may be removed from a port of the adapter coupled to the extension tube and the port may be disinfected and/or a needleless connector or PRN may be attached to the port.

In some embodiments, another vascular access system may include a cannula assembly, which may include a cannula hub and a cannula extending distally from the cannula hub. In some embodiments, the vascular access system may include a housing, which may include a distal opening, a proximal opening, a lumen extending from the distal opening to the proximal opening, and an internal rib. In some embodiments, the housing may include a notch disposed distal to the internal rib. In some embodiments, a height of the internal rib may increase in a distal direction.

In some embodiments, the cannula hub may be disposed within the proximal opening of the housing. In some embodiments, a distal end of the cannula may be disposed proximal to the distal opening.

In some embodiments, the housing may include a slot, which may extend from the distal opening. In some embodiments, the housing may include a stepped surface. In some embodiments, the cannula hub may include a flange, which may contact the stepped surface. In some embodiments, the stepped surface may form the proximal opening of the housing. In some embodiments, the other vascular access system may include the catheter assembly.

In some embodiments, in response to moving the cannula hub distally within the housing along the internal rib, the cannula may extend through the septum and an inner diameter of the housing may increase as the internal rib bends outwardly. In some embodiments, in response to the internal rib bending outwardly, the protrusion may be released from the notch.

It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 5A is an upper perspective view of an example catheter system, illustrating an example catheter assembly prior to coupling with an example cannula assembly, according to some embodiments;

FIG. 5B is an upper perspective view of the cannula assembly of FIG. 5A, according to some embodiments;

DESCRIPTION OF EMBODIMENTS

Figure 1A:
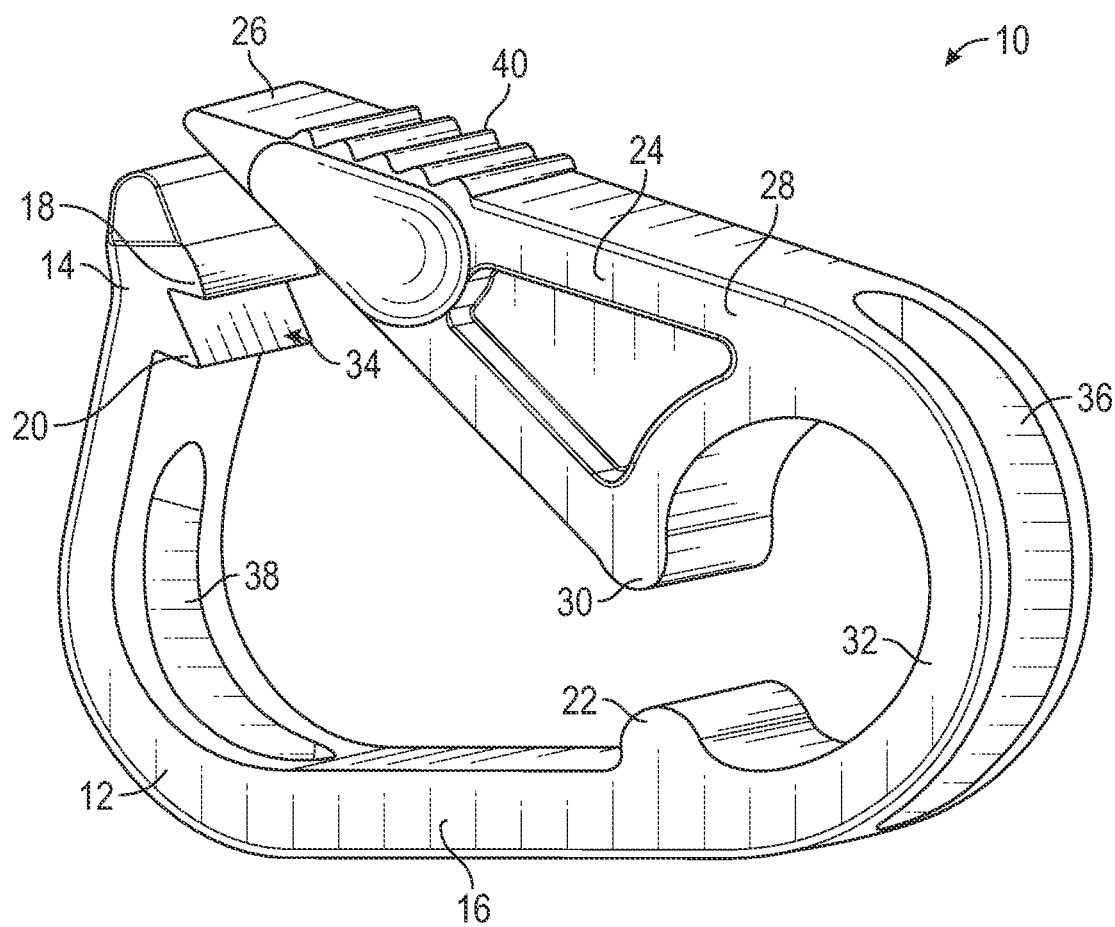
FIG. 1A is an upper perspective view of an example pinch clamp device, according to some embodiments.
Figure 1B:
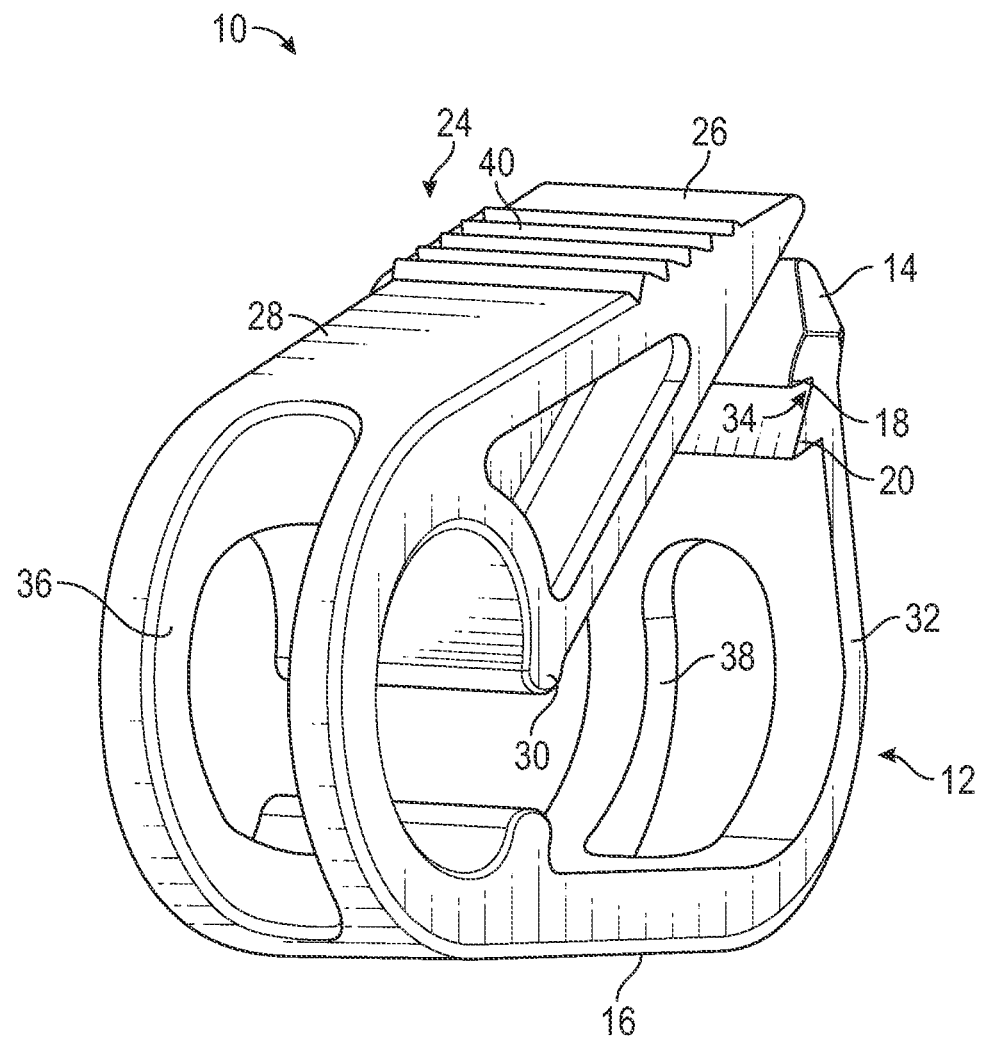
FIG. 1B is another upper perspective view of the pinch clamp device of FIG. 1A, according to some embodiments.

Referring now to FIGS. 1A-1B, a pinch clamp device 10 is illustrated, according to some embodiments. In some embodiments, the pinch clamp device 10 may include a first arm 12, which may include a first end 14 and a second end 16. In some embodiments, the first end 14 may include a first lip 18 and a second lip 20. In some embodiments, the second end 16 may include a first clamping surface 22. In some embodiments, the first lip 18 and/or the second lip 20 may include a ridge or ledge. In some embodiments, the first lip 18 and the second lip 20 may be parallel. In some embodiments, a width of the first lip 18 and/or a width of the second lip 20 may be approximately equal to a width of the pinch clamp device 10.

In some embodiments, the pinch clamp device 10 may include a second arm 24, which may include a first end 26 and a second end 28. In some embodiments, the first end 26 may include a terminal end. In some embodiments, the second end 28 may include a second clamping surface 30 positioned opposite the first clamping surface 22. In some embodiments, the pinch clamp device 10 may include a hinge 32 interconnecting the second end 16 of the first arm 12 and the second end 28 of the second arm 24.

In some embodiments, the first end 26 of the second arm 24 may be configured to engage with the first lip 18 to secure the pinch clamp device 10 in a first engaged configuration. In some embodiments, the first end 26 of the second arm 24 may be configured to engage with the second lip 20 to secure the pinch clamp device 10 in a second engaged configuration. In some embodiments, the second arm 24 may be tensioned or biased inwardly a first amount to engage with the first lip 18. In some embodiments, the second arm 24 may be tensioned or biased inwardly a second amount to engage with the second lip 20. In some embodiments, the second amount may be greater than the first amount. FIGS. 1A-1B illustrated the pinch clamp device 10 in a relaxed or disengaged configuration, according to some embodiments. In some embodiments, the pinch clamp device 10 may be constructed of a rigid or semi-rigid material.

In some embodiments, the first end 26 of the second arm 24 may include a wedged or tapered shape such that the first end 26 tapers inwardly to a tip. In some embodiments, there may be a gap 34 between the first lip 18 and the second lip 20. In some embodiments, the gap 34 may be V-shaped or another suitable shape to securely engage with the first end 26 of the second arm 24.

In some embodiments, the first clamping surface 22 and/or the second clamping surface 30 may include a raised surface having a width approximately equal to the width of the pinch clamp device 10. In some embodiments, the first clamping surface 22 and/or the second clamping surface 30 may be planar or generally flat. In some embodiments, the first clamping surface 22 and/or the second clamping surface 30 may be angled, rounded, pointed, ridged, grooved, or another suitable shape.

In some embodiments, the hinge 32 may include a rounded extension of the second end 16 of the first arm 12 and the second end 28 of the second arm 24. In some embodiments, the hinge 32 may include a window or opening 36, through which extension tube may be passed. In some embodiments, the first arm 12 may include a window or opening 38, which may be generally aligned with the opening 36 and which may be configured to accommodate the extension tube.

In some embodiments, a contact or exterior surface of the second arm 24 may include a grip feature 40. The grip feature 40 may increase friction between a user's thumb or finger and the pinch clamp device 10 during use. In some embodiments, the grip feature 40 may include multiple ridges or raised features, which may be parallel.

Figure 1C:
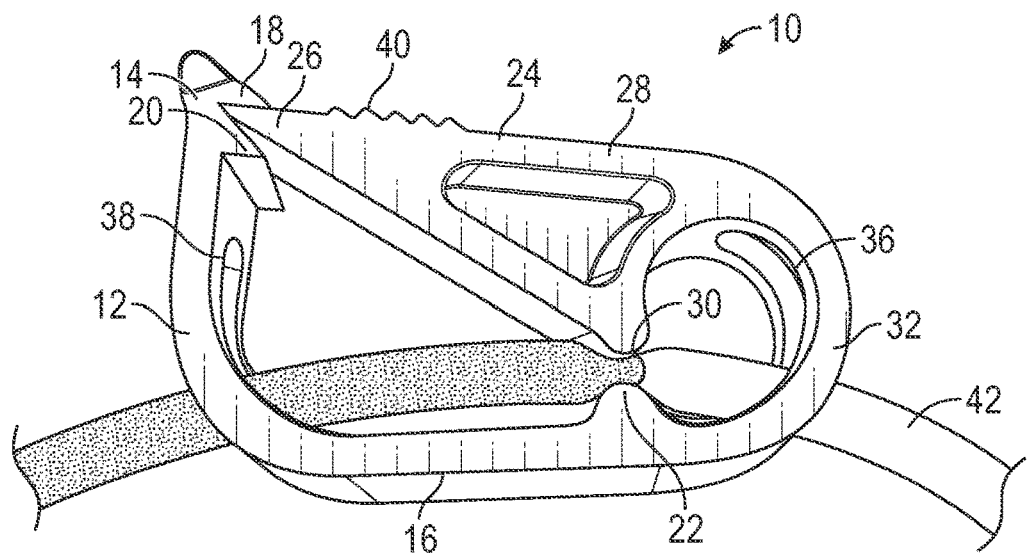
FIG. 1C is a side view of the pinch clamp device of FIG. 1A, illustrating the pinch clamp device in a first engaged configuration, according to some embodiments.
Figure 1D:
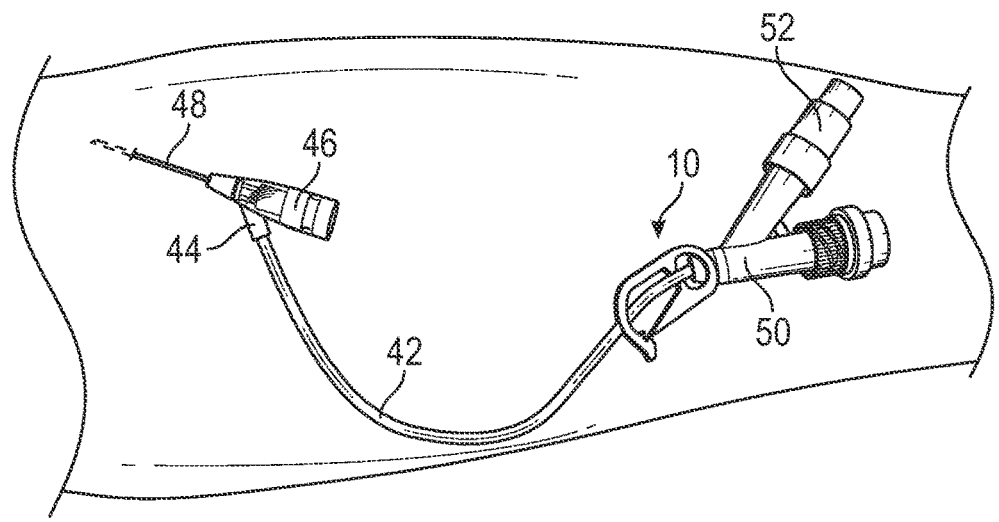
FIG. 1D is an upper perspective view of an example catheter assembly inserted into a patient, according to some embodiments.

Referring now to FIG. 1C-1D, in some embodiments, extension tube 42 of a catheter assembly may extend through the pinch clamp device 10. In some embodiments, the catheter assembly may include a peripheral intravenous catheter ("PIVC") system. In some embodiments, the catheter system may include a peripherally inserted central catheter ("PICC") system or a midline catheter system.

In some embodiments, the extension tube 42 may extend from a side port 44 of a catheter adapter 46 and through the pinch clamp device 10. In some embodiments, a catheter 48 may extend distally from the catheter adapter 46. In some embodiments, a proximal end of the extension tube 42 may be coupled to an adapter 50, which may include one or more ports. In some embodiments, a vent plug 52 may be coupled to at least one port of the adapter 50. In some embodiments, a needleless connector may be coupled to at least one port of the adapter 50. In some embodiments, a needle assembly that includes an introducer needle (not illustrated) may be used to insert the catheter 48 into an arm or another suitable location of the patient, and then the needle assembly may be removed from the catheter adapter 46.

FIGS. 1C-1D illustrate the pinch clamp device 10 in the first engaged configuration, according to some embodiments. In some embodiments, the first end 26 of the second arm 24 may be configured to engage with the first lip 18 to partially occlude the extension tube 42 such that air passes through the extension tube 42 but blood does not. In some embodiments, in response to the first end 26 of the second arm 24 being engaged with the second lip 20, the pinch clamp may be configured to occlude the extension tube 42 such that neither air nor blood pass through the extension tube 42.

Figure 2:
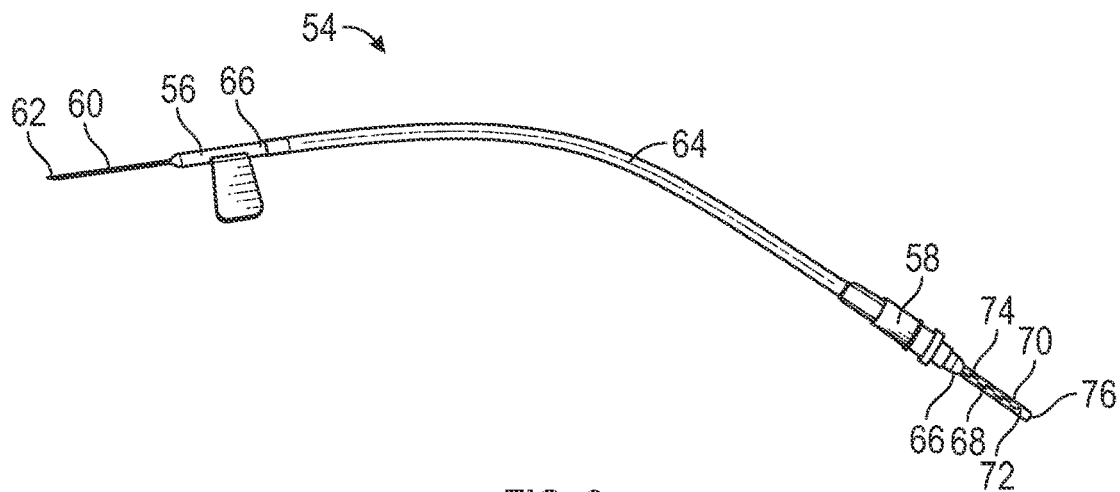
FIG. 2 is an upper perspective view of an example winged needle set, according to some embodiments.

Referring now to FIG. 2, a winged needle set 54 is illustrated, according to some embodiments. In some embodiments, the winged needle set 54 may include a cannula hub 56. In some embodiments, the cannula hub 56 may include a wing or tab 92, which may extend outwardly from a body of the cannula hub 56. In some embodiments, a cannula 60 may extend distally from the cannula hub 56. In some embodiments, the cannula 60 may include a distal tip 62. In some embodiments, a lumen may extend through the winged needle set 54.

In some embodiments, the winged needle set 54 may include an extension tube 64 coupled to a proximal end 66 of the cannula hub 56. In some embodiments, a blood collection device may be coupled to an adapter 58 disposed at a proximal end of the extension tube 64. In some embodiments, the adapter 58 may include any suitable adapter to connect with the blood collection device. In some embodiments, another cannula 68 may extend in a proximal direction from the adapter 58. In some embodiments, an elastomeric sheath 70 may be coupled to the adapter 58, and a proximal end 72 of the other cannula 68 may be enveloped within the elastomeric sheath 70. In some embodiments, the elastomeric sheath 70 may include an open distal end 74 and a closed proximal end 76.

In some embodiments, in response to a blood collection device (not illustrated) pushing the elastomeric sheath 70 distally, the other cannula 68 may pierce the elastomeric sheath 70, and the other cannula 68 may insert into the blood collection device. In some embodiments, the blood collection device may include a blood collection tube or VACUTAINER tube, which may include a hermetic seal at an open end and a vacuum. The vacuum in the VACUTAINER tube may cause the blood sample to be drawn, through at least a portion of a catheter.

Figure 3A:
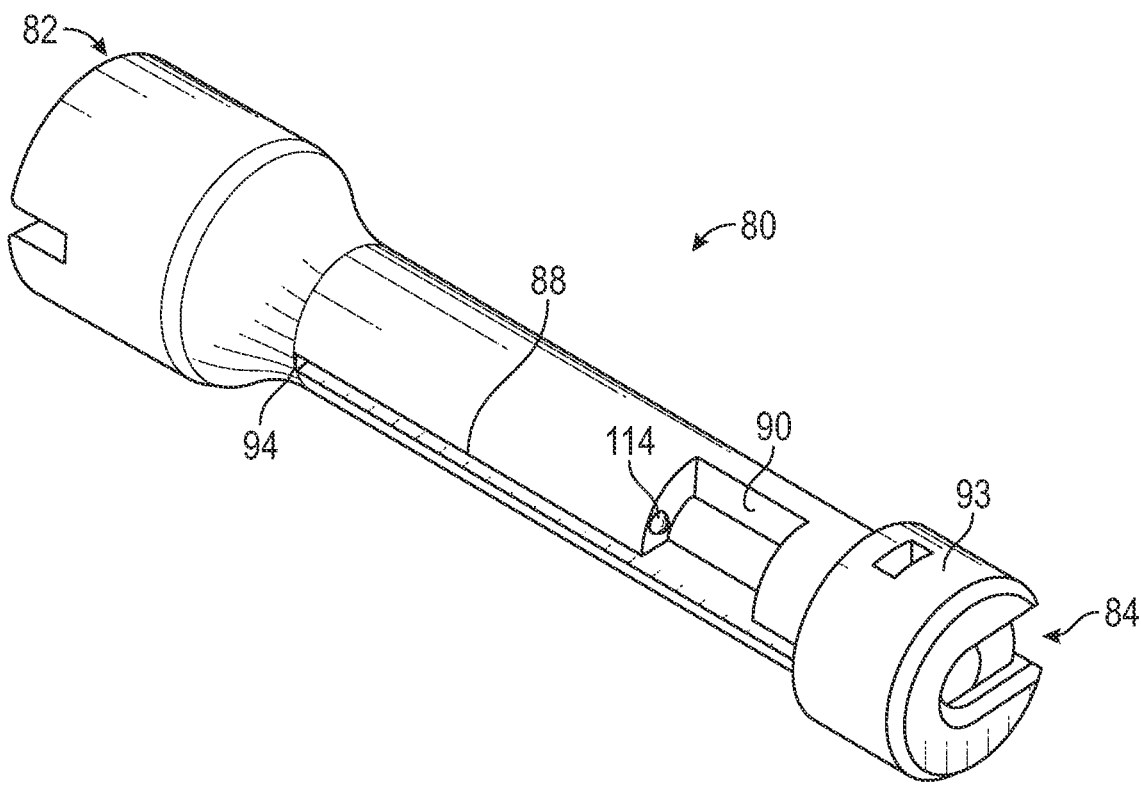
FIG. 3A is an upper perspective view of an example housing, according to some embodiments.
Figure 3B:
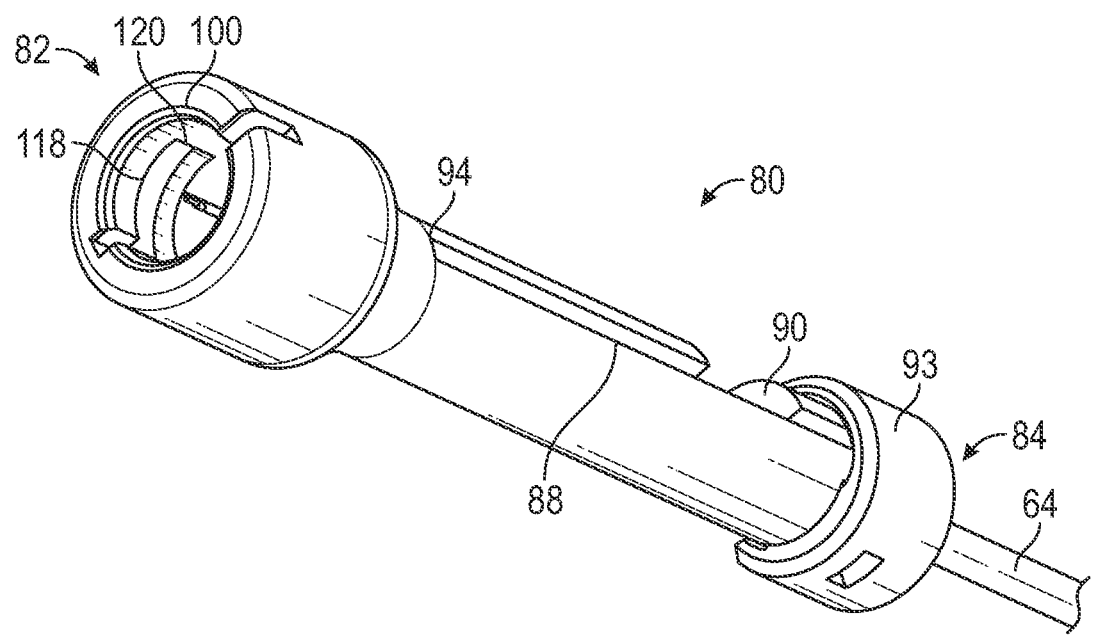
FIG. 3B is a lower perspective view of the housing of FIG. 3A, with the winged needle set of FIG. 2 disposed inside the housing, according to some embodiments.
Figure 3C:
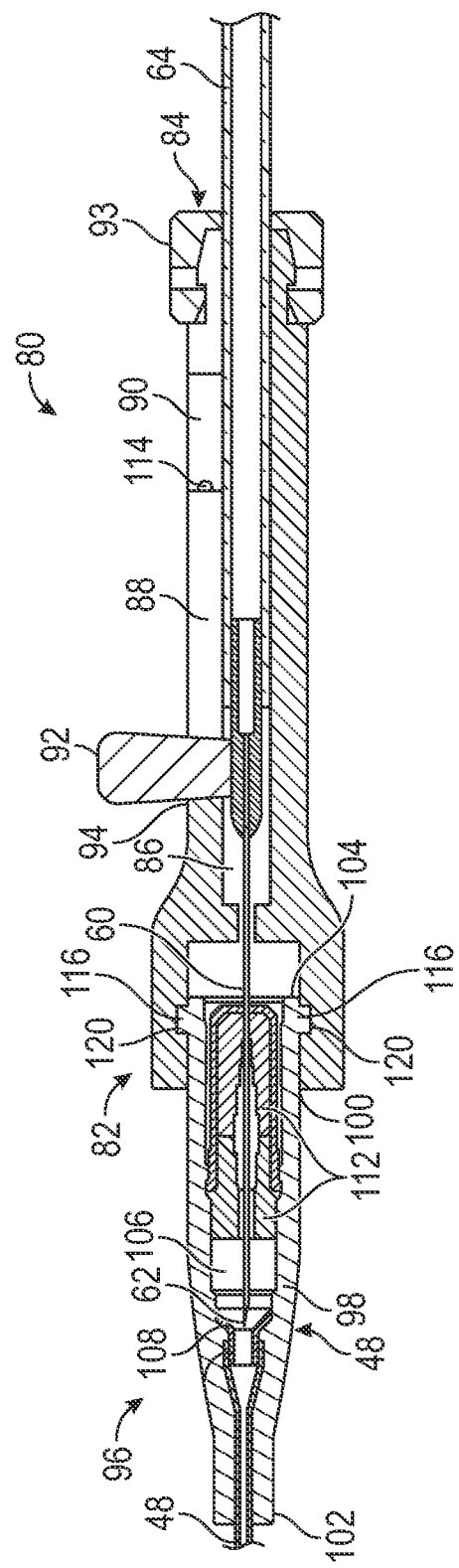
FIG. 3C is a cross-sectional view of an example catheter system, according to some embodiments.

Referring now to FIG. 3A-3C, a housing 80 may include a distal end 82, a proximal end 84, and a lumen 86 extending between the distal end 82 and the proximal end 84. In some embodiments, the housing 80 may include a slot 88 disposed between the distal end 82 and the proximal end 84. In some embodiments, a distal portion of the slot 88 may be linear and configured to guide the tab. In some embodiments, the distal portion of the slot 88 may include a width slightly greater than a width of the tab 92. In some embodiments, the slot 88 may include a notch 90, which may be proximal to the distal portion of the slot 88.

In some embodiments, the extension tube 64 of the winged needle set 54 may extend through the proximal end 84 of the housing 80, which may include an opening. In some embodiments, the proximal end 84 of the housing 80 may include a cap 93. In some embodiments, the cap 93 may be coupled to the housing 80 after the winged needle set 54 is placed inside the housing 80. In some embodiments, the cap 93 may be coupled to the housing 80 via threads, a snap fit, or another suitable mechanism. In some embodiments, the cap 93 may be permanently or selectively coupled to the housing 80.

In some embodiments, the winged needle set 54 may be disposed within the lumen 86 of the housing 80 and movable with respect to the slot 88. In some embodiments, the cannula hub 56 may include a tab 92, which may extend from the body of the cannula hub 56 through the slot 88. In some embodiments, the tab 92 may be configured to be gripped by a user to advance or retract the winged needle set 54. In some embodiments, in response to the tab 92 being disposed within or even with the notch 90, the distal tip 62 of the cannula 60 may be disposed within the housing 80, protecting the user from accidental cannula stick. In some embodiments, in response to advancing the tab 92 along the slot 88 to a distal end 94 of the slot 88, the distal tip 62 of the cannula 60 may be disposed distal to the distal end 82 of the housing 80.

In some embodiments, the housing 80 may be coupled to a catheter assembly 96, which may include or correspond to a catheter assembly similar to that illustrated in FIG. 1D. In some embodiments, the catheter adapter 46 may include a body 98 disposed within a distal opening 100 of the distal end 82 of the housing 80. In some embodiments, the body 98 may include a distal end 102, a proximal end 104, a lumen 106 extending through the distal end 102 of the body 98 and the proximal end 104 of the body 98. In some embodiments, the proximal end 104 of the body 98 may be coupled to the distal end 82 of the housing 80. In some embodiments, the catheter 48 may extend from the distal end 102 of the body 98 of the catheter adapter 46 and may be secured within the catheter adapter 46.

In some embodiments, the catheter adapter 46 may include the side port 44. In some embodiments, the catheter assembly 96 may include a pinch clamp device, such as, for example, the pinch clamp device 10 discussed with respect to FIGS. 1A-1D. In some embodiments, the extension tube 42 may extend from the side port 44 through the pinch clamp device 10.

In some embodiments, the catheter assembly 96 may include a wedge 108 disposed within the lumen 106 of the catheter adapter 46. In some embodiments, in response to advancing the tab 92 along the slot 88 to the distal end 94 of the slot 88, the distal tip 62 of the cannula 60 may be disposed within the wedge 108. In some embodiments, the wedge 108 may be constructed of a rigid or semi-rigid material. In some embodiments, the wedge 108 may be constructed of metal, which may prevent damage to the catheter adapter 46 by the distal tip 62. In some embodiments, the wedge 108 may secure the catheter 48 within the catheter adapter 46.

In some embodiments, a septum 112 may be disposed within the lumen 106 of the catheter adapter 46. In some embodiments, a side of the notch 90 may include a protrusion 114, which may provide resistance to rotation of the tab 92 outside the notch 90. In some embodiments, in response to advancing the tab 92 along the slot 88, the cannula 60 may extend through the septum 112. For example, in response to advancing the tab 92 along the slot 88 to the distal end 94 of the slot 88, the cannula 60 may extend through the septum 112. In some embodiments, when the cannula 60 is inserted through the septum 112, the catheter system may be configured to collect blood, which may flow from the patient, through the catheter 48 into the catheter adapter 46, into the cannula 60, and into the extension tube 64. In some embodiments, from the extension tube 64 the blood may flow into the adapter 50 (illustrated, for example, in FIG. 1D) and the blood collection device coupled to the adapter 50.

In some embodiments, the housing 80 may facilitate blood draw through the septum 112 via a straight pathway, which may reduce a risk of hemolysis. Also, in some embodiments, blood draw through the septum 112, facilitated by the housing 80, may reduce a length of a fluid pathway between the catheter 48 and the blood collection device and thereby reduce a risk of blood coagulation in a middle of the fluid pathway and insufficient blood volume for a blood sample. In some embodiments, the housing 80 may provide a safety shield in which the distal tip 62 may be disposed to protect the user. In some embodiments, when the housing 80 is coupled to the catheter adapter 46, the user may be protected before, during, and after blood draw from the distal tip 62, which may be sharp. In some embodiments, air may be vented in the catheter system via the vent plug 52, and the catheter system may be closed to prevent bacterial contamination.

In some embodiments, the housing 80 may be coupled to the catheter adapter 46 in various ways. In some embodiments, an outer surface of the body 98 of the catheter adapter 46 may include one or more protrusions 116. In some embodiments, an inner surface of the housing may include one or more L-shaped slots 118, which may extend from the distal end 82 of the housing 80. In some embodiments, coupling the housing 80 to the proximal end 104 of the catheter adapter 46 may include inserting the protrusions 116 into the L-shaped slots 118 and rotating the housing 80 or the catheter adapter 46 to position the protrusions 116 at ends 120 of the L-shape slots 118. In some embodiments, housing 80 or the catheter adapter 46 may be rotated approximately 90 degrees to position the protrusions 116 at ends 120 of the L-shape slots 118.

Referring now to FIGS. 4A-4H, in some embodiments, a method, which may be used to collect blood from a patient, may include positioning the pinch clamp device 10 at a proximal end 117 of the extension tube 42. In some embodiments, after positioning the pinch clamp device 10 at the proximal end 117 of the extension tube 42, the catheter 48 may be inserted into vasculature of the patient. In some embodiments, when the catheter 48 is inserted in the vasculature of the patient, blood may flow slowly in a proximal direction through the catheter 48 and stop at the pinch clamp device 10. In some embodiments, because the pinch clamp device 10 is in the first engaged configuration, air may pass the pinch clamp device 10, and the catheter 48 and the extension tube 42 may be primed.

In some embodiments, after inserting the catheter 48 into vasculature of the patient, the proximal end 104 of the catheter adapter 46 may be disinfected. In some embodiments, after disinfecting the proximal end 104 of the catheter adapter 46, the housing 80 may be coupled to the proximal end 104 of the catheter adapter 46.

In some embodiments, after coupling the housing 80 to the proximal end 104 of the catheter adapter 46, the tab 92 may be advanced along the slot 88 to the distal end 94 of the slot 88. The cannula hub 56 and the winged needle set 54 may be advanced with the tab 92. In some embodiments, the tab 92 may be disposed within the notch 90, as illustrated, for example, in FIG. 4A. In some embodiments, in order to advance the tab 92 distally, the tab 92 may be rotated out of the notch 90, as illustrated, for example, in FIG. 4B. In some embodiments, the tab 92 may be advanced distally along the slot 88 as illustrated, for example, in FIG. 4C. In some embodiments, in response to advancing the tab 92 along the slot 88 to the distal end 94 of the slot 88, the distal tip 62 of the cannula 60 may pass through a septum disposed within the lumen of the catheter adapter 46 and/or may be disposed within a wedge. Thus, in some embodiments, the distal end 94 of the slot 88 may serve as an indicator to the user of a position of the distal tip 62 of the cannula 60.

Figure 4A:
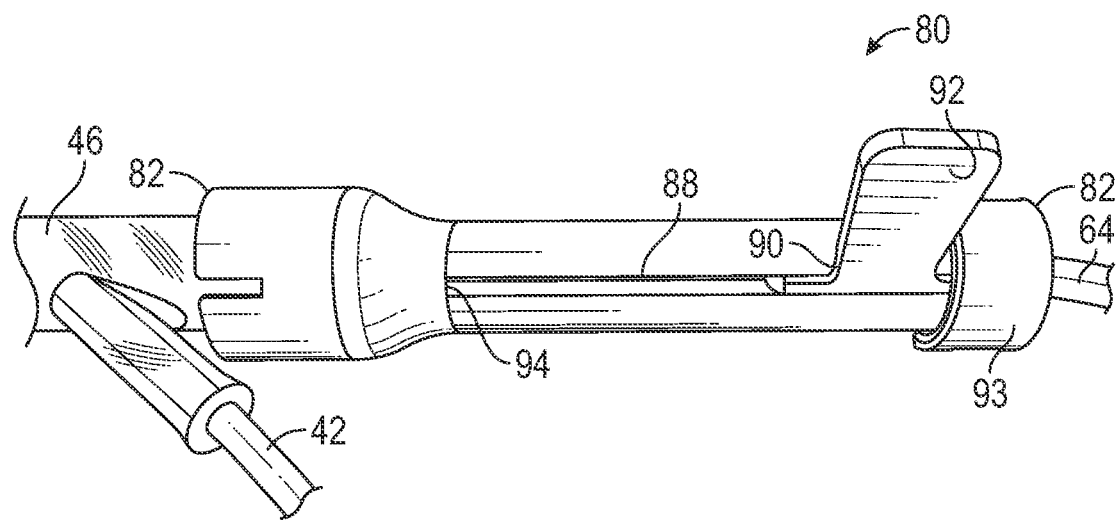
FIG. 4A is an upper perspective view of the catheter system of FIG. 3C illustrating an example tab disposed within an example notch, according to some embodiments.
Figure 4B:
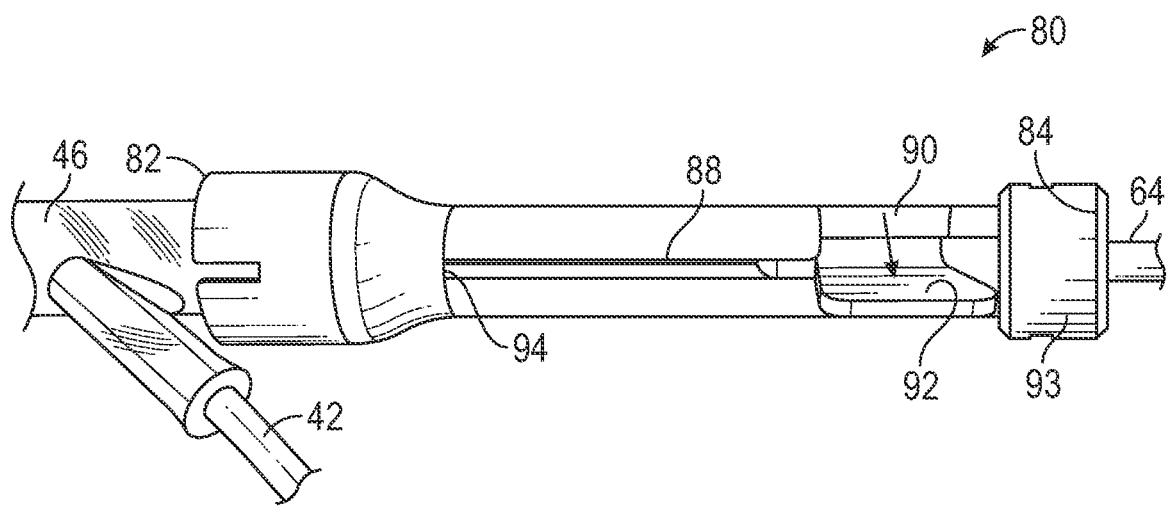
FIG. 4B is an upper perspective view of the catheter system of FIG. 3C, illustrating the tab rotated away from the notch, according to some embodiments.
Figure 4C:
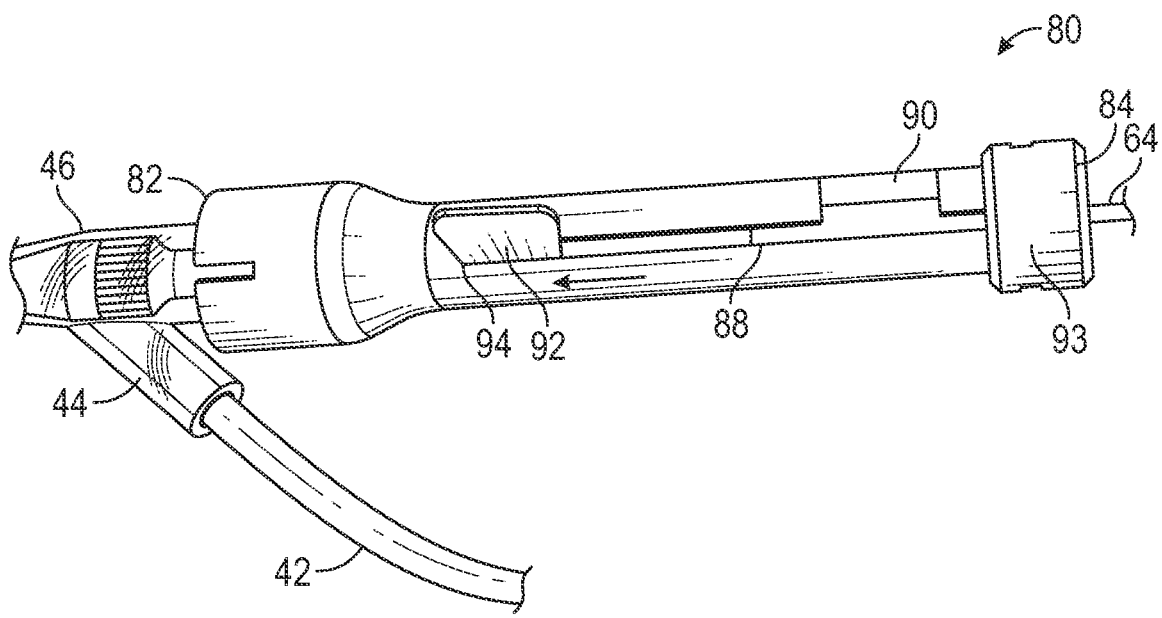
FIG. 4C is an upper perspective view of the catheter system of FIG. 3C, illustrating the tab in an advanced position, according to some embodiments.
Figure 4D:
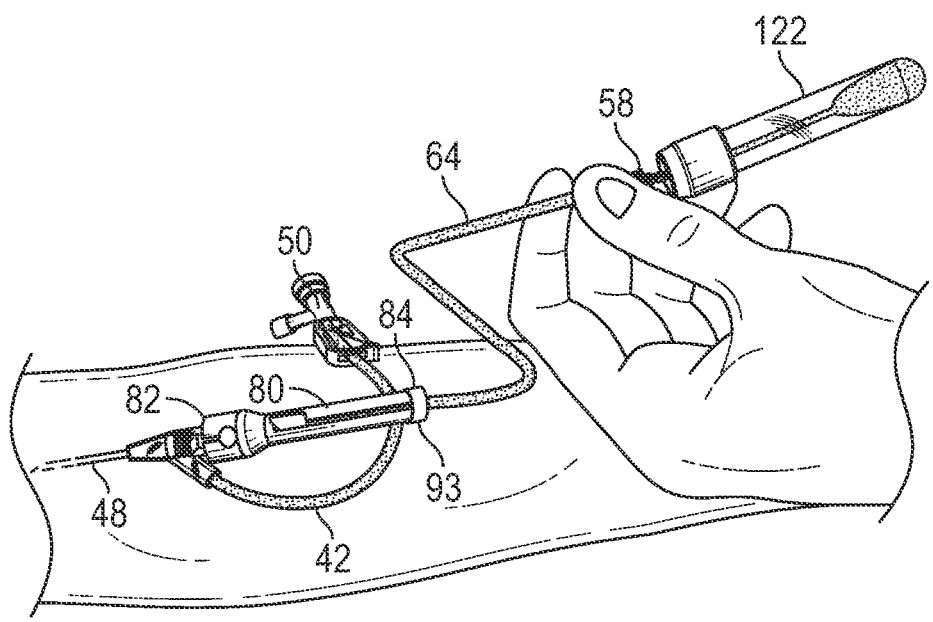
FIG. 4D is an upper perspective view of the catheter system of FIG. 3C, illustrating blood being drawn from the patient, according to some embodiments.
Figure 4E:
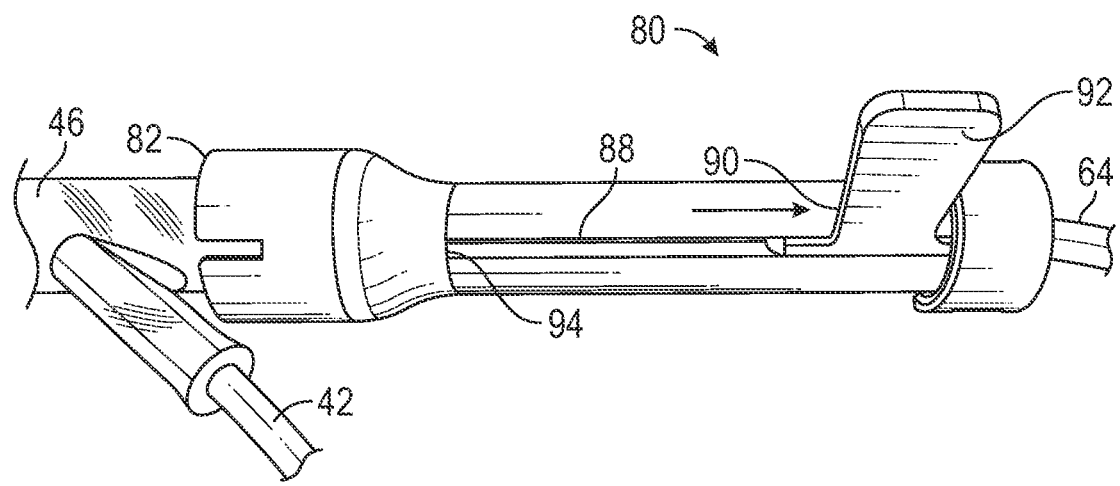
FIG. 4E is an upper perspective view of the catheter system of FIG. 3C, illustrating the tab in a retracted position and rotated into the notch, according to some embodiments.

In some embodiments, after the housing 80 is coupled to the proximal end of the catheter adapter 46, blood may be drawn through the cannula 60, as illustrated, for example, in FIG. 4D. In some embodiments, after blood is drawn through the cannula 60 and collected in the blood collection device 122, the tab 92 may be moved along the slot 88 from the distal end 94 of the slot 88 into the notch 90, as illustrated, for example, in FIG. 4E. In some embodiments, the tab 92 may be rotated into the notch 90, where movement of the tab 92 in a distal and/or proximal direction may be prevented.

In some embodiments, in response to moving the tab 92 along the slot 88 from the distal end 94 of the slot 88 into the notch 90, the distal tip 62 of the cannula 60 may be retracted into the housing 80. In some embodiments, after the cannula 60 is retracted into the housing 80, the housing 80 may be uncoupled from the proximal end 104 of the catheter adapter 46. In some embodiments, the housing 80 may be uncoupled from the proximal end 104 of the catheter adapter 46 by rotating the housing 80 such that the protrusions 116 are removed from the L-shaped slots 118.

Figure 4F:
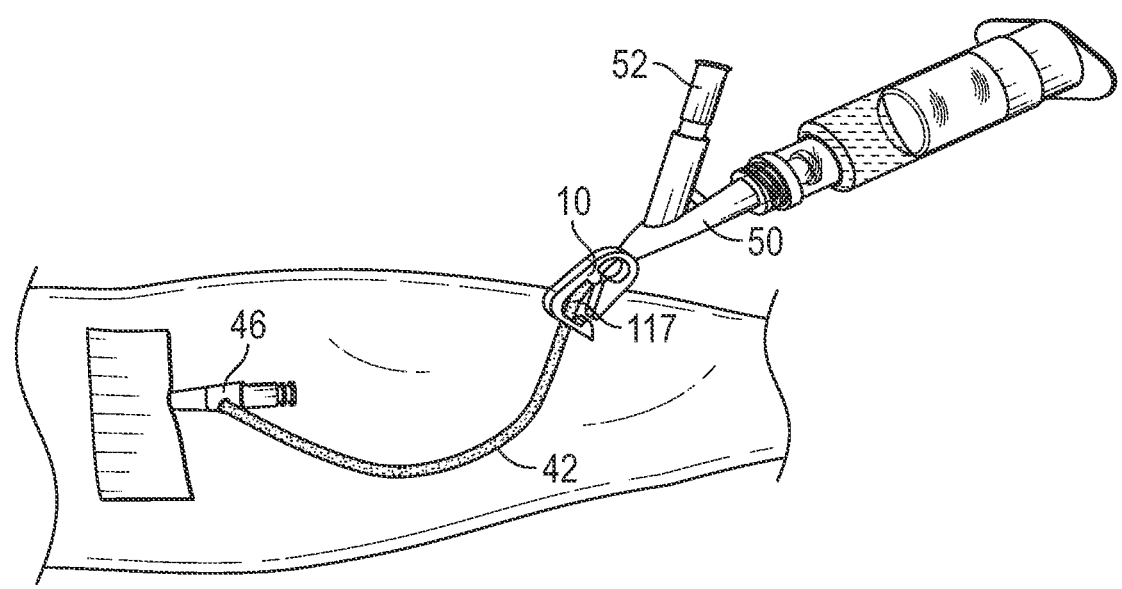
FIG. 4F is an upper perspective view of the catheter system of FIG. 3C, illustrating flushing of an example adapter, according to some embodiments.
Figure 4G:
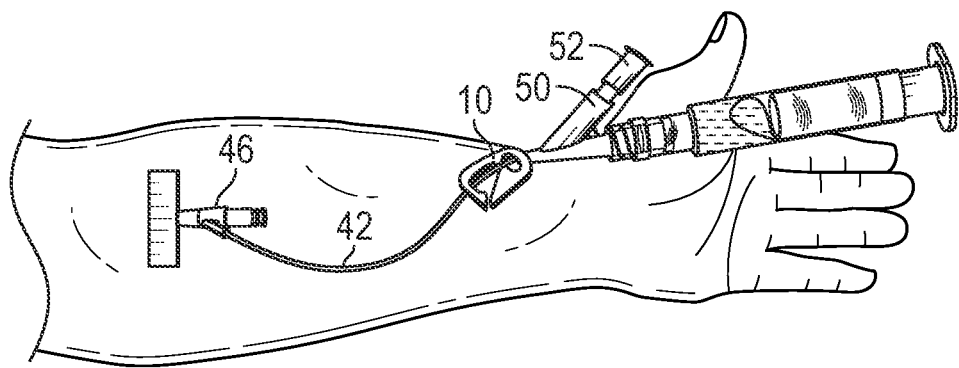
FIG. 4G is an upper perspective view of the catheter system of FIG. 3C, illustrating flushing of an example catheter, according to some embodiments.
Figure 4H:
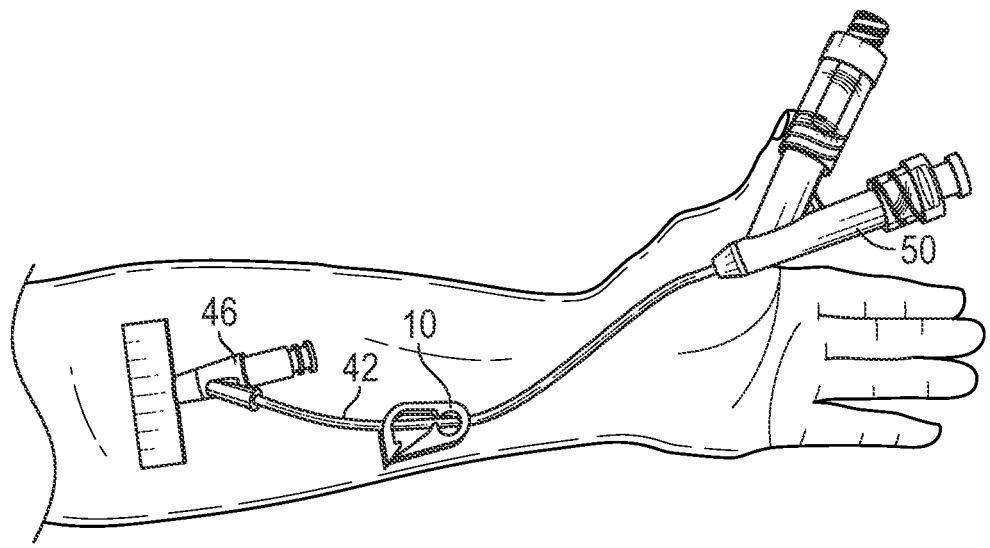
FIG. 4H is an upper perspective view of the catheter system of FIG. 3C, illustrating an example needleless connector coupled to the adapter, according to some embodiments.

In some embodiments, after the housing 80 is uncoupled from the proximal end 104 of the catheter adapter 46, the adapter 50 may be flushed, as illustrated, for example, in FIG. 4F. In some embodiments, after the adapter 50 is flushed, the first end 26 of the pinch clamp device 10 may be disengaged from the first lip 18 such that the pinch clamp device 10 is in an open or relaxed configuration. In some embodiments, when the pinch clamp device 10 is in the open configuration, the catheter 48 may be flushed via the extension tube 42, as illustrated, for example, in FIG. 4G. In some embodiments, after the catheter 48 is flushed, the vent plug 52 may be removed from a port of the adapter 50 coupled to the extension tube 42 and the port may be disinfected and/or a needleless connector or PRN may be attached to the port, as illustrated, for example, in FIG. 4H.

Referring now to FIGS. 5A-5G, in some embodiments, a cannula assembly 124 may include a cannula hub 126 and a cannula 128 extending distally from the cannula hub 126. In some embodiments, a cover or housing 130 may include a distal opening 132, a proximal opening 134, a lumen 136 extending from the distal opening 132 to the proximal opening 134, and an internal rib 138. In some embodiments, the housing 130 may include a notch 140 disposed distal to the internal rib 138. In some embodiments, a height of the internal rib 138 may increase in a distal direction. In some embodiments, the cannula hub 126 may be disposed within the proximal opening 134 of the housing 130. In some embodiments, a distal end 142 of the cannula 128 may be disposed proximal to the distal opening 132.

In some embodiments, the housing 130 may include a slot 144, which may extend from the distal opening 132. In some embodiments, the housing 130 may include a stepped surface 146. In some embodiments, the cannula hub 126 may include a flange 148, which may contact the stepped surface 146, as illustrated, for example, in FIGS. 5B-5D. In some embodiments, the flange 148 and the stepped surface 146 may be annular. In some embodiments, the stepped surface 146 may form the proximal opening 134 of the housing 130.

In some embodiments, a catheter assembly 150 may be coupled to the cannula assembly 124. In some embodiments, the catheter assembly 150 may include or correspond to the catheter assembly 96 discussed with respect to FIGS. 3A-3C. In some embodiments, a catheter adapter 46 of the catheter assembly 150 may include a protrusion 152, which may be inserted into the notch 140 to couple the catheter assembly 150 to the cannula assembly 124.

In some embodiments, in response to moving the cannula hub 126 distally within the housing 130 along the internal rib 138, the cannula 128 may extend through the septum 112 and an inner diameter of the housing 130 may increase as the internal rib 138 bends outwardly. In some embodiments, the slot 144 may facilitate expansion of the housing 130 outwardly and increase of the inner diameter of the housing 130. In some embodiments, in response to the internal rib 138 bending outwardly, the protrusion 152 may be released from the notch 140, as illustrated, for example, in FIG. 5E.

In some embodiments, the catheter assembly 150 may be removed from the patient when the catheter assembly 150 is coupled to the cannula assembly 124. In some embodiments, the catheter assembly 150 may be removed from the vasculature of the patient when the catheter assembly 150 is coupled to the cannula assembly 124 and the cannula 128 is inserted through the septum 112. In these embodiments, the user may grip the housing 130 with the cannula hub 126 in an advanced position, illustrated, for example, in FIG. 5E. In some embodiments, after the catheter assembly 150 and the cannula assembly 124 are removed from the vasculature of the patient, the cannula assembly 124 may be withdrawn from the catheter assembly 150, as illustrated, for example, in FIG. 5F, and the cannula hub 126 may be retracted within the housing 130 in a proximal direction such that the distal end 142 is disposed within the housing 130.

A method of collecting blood using the catheter assembly 150 and the housing 130 may include one or more steps of the method described with respect to FIGS. 4A-4H. In some embodiments, the method of collecting blood using the catheter assembly 150 and the housing 130 may include positioning a pinch clamp device, such as the pinch clamp device 10 described with respect to FIGS. 1A-4D, at a proximal end of the extension tube 42. In some embodiments, after positioning the pinch clamp device at the proximal end of the extension tube 42, the catheter assembly 150 may be coupled to the housing 130 and inserted into vasculature of the patient. In some embodiments, when the catheter 48 is inserted in the vasculature of the patient, blood may flow slowly in a proximal direction through the catheter 48 and stop at the pinch clamp device. In some embodiments, because the pinch clamp device is in the first engaged configuration, air may pass the pinch clamp device, and the catheter 48 and the extension tube 42 may be primed.

Figure 5C:
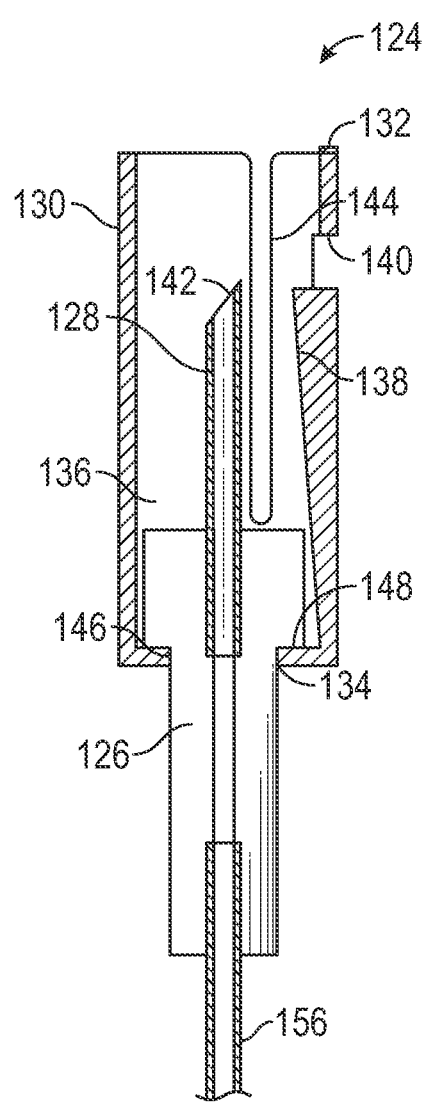
FIG. 5C is a cross-sectional view of the cannula assembly of FIG. 5A, according to some embodiments.
Figure 5D:
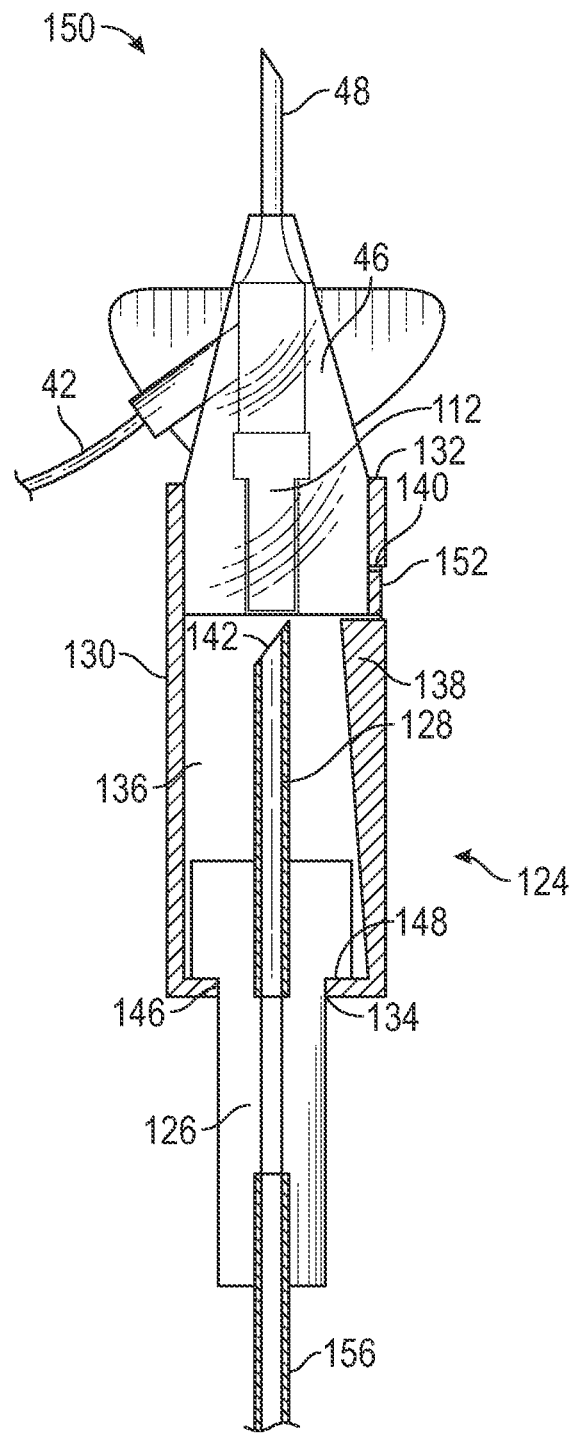
FIG. 5D is a cross-sectional view of the catheter system of FIG. 5A, illustrating an example cannula hub in a retracted position, according to some embodiments.
Figure 5E:
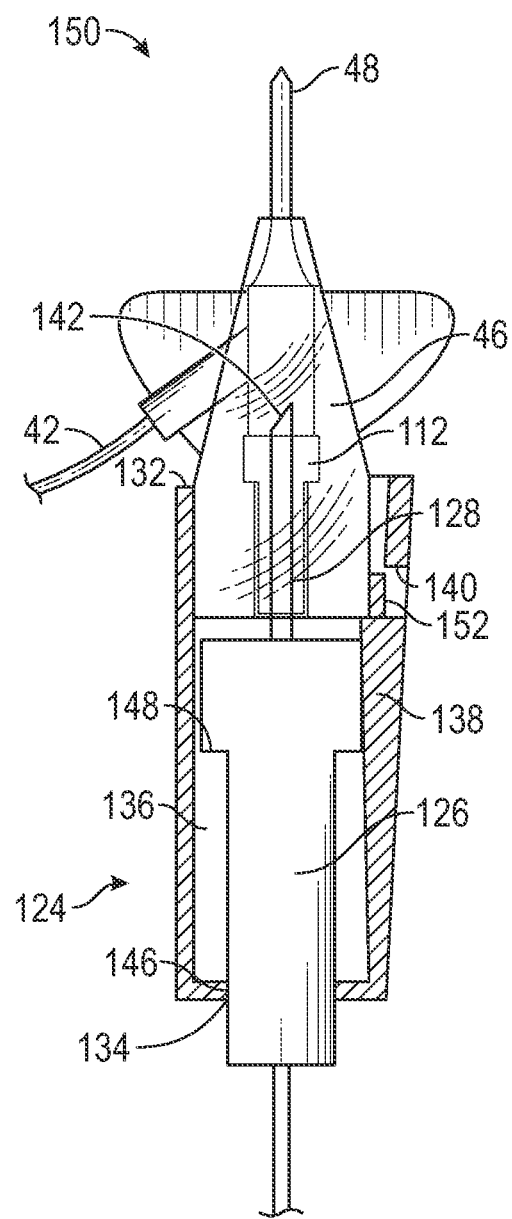
FIG. 5E is a partial cutaway view of the catheter system of FIG. 5A, illustrating the cannula hub in an advanced position, according to some embodiments.
Figure 5F:
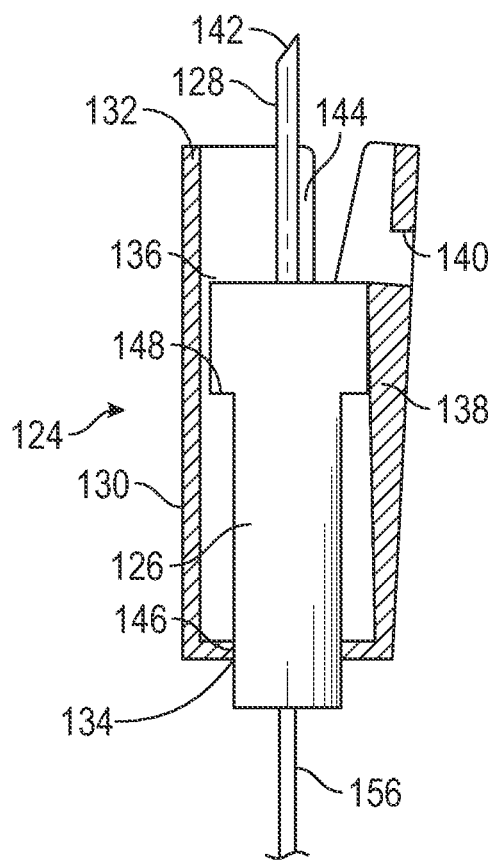
FIG. 5F is a partial cutaway view of the cannula assembly of FIG. 5A, illustrating the cannula hub in the advanced position, according to some embodiments.
Figure 5G:
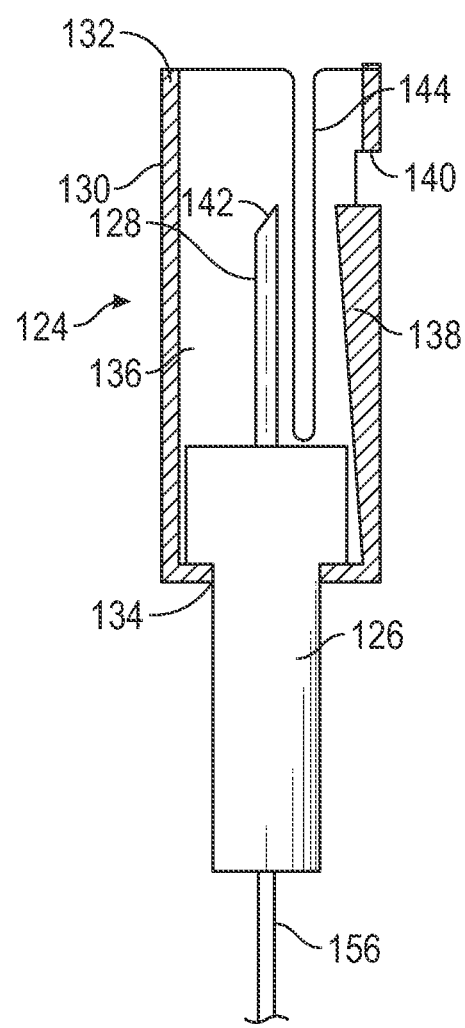
FIG. 5G is a partial cutaway view of the cannula assembly of FIG. 5A, illustrating the cannula hub in a retracted position, according to some embodiments.

In some embodiments, after the catheter assembly 150 is coupled to the housing 130 and inserted into vasculature of the patient, the user may advance the cannula hub 126 in the distal direction such that the cannula 128 is inserted through the septum 112, as illustrated, for example, in FIG. 5E.

In some embodiments, in response to the cannula 128 being inserted through the septum 112, blood may be drawn through the cannula 128. In some embodiments, a blood collection device, such as, for example, the blood collection device 122 described with respect to FIGS. 4D, may be coupled to an adapter 154. In some embodiments, the cannula assembly 124 may include an extension tube 156, which may be coupled to the adapter 154 and the cannula hub 126. In some embodiments, a distal end of the extension tube 156 may be integrated with the cannula hub 126 and/or a proximal end of the extension tube 156 may be integrated with the adapter 154. In some embodiments, the adapter 154 may include or correspond to the cannula hub 56 described with respect to FIG. 2.

In some embodiments, after the housing 130 is uncoupled from the proximal end of the catheter adapter 46, an adapter disposed at the proximal end of the extension tube 42 may be flushed. In some embodiments, after the adapter is flushed, the pinch clamp device may be moved from the first engaged configuration to an open or relaxed configuration to flush the catheter 48.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

We claim:

1. A vascular access system, comprising:
   a cannula assembly, comprising a cannula hub and a cannula extending distally from the cannula hub; and
   a housing, comprising a distal opening, a proximal opening, a lumen extending from the distal opening to the proximal opening, an internal rib, and a notch disposed distal to the internal rib, wherein a height of the internal rib increases in a distal direction, wherein the cannula hub is disposed within the proximal opening, wherein a distal end of the cannula is disposed proximal to the distal opening;
   a catheter adapter, comprising:
      a body disposed within the distal opening, wherein the body comprises a distal end, a proximal end, a lumen extending through the distal end and the proximal end; and
   a protrusion extending from an outer surface of the body, wherein the protrusion is disposed within the notch;
      a septum disposed within the lumen of the body of the catheter adapter; and
      a catheter extending from the distal end of the body of the catheter adapter, wherein in response to moving the cannula hub distally within the housing along the internal rib, the catheter extends through the septum and an inner diameter of the housing increases and the protrusion is released from the notch.

2. The vascular access system of claim 1, wherein the housing further comprises a slot extending from the distal opening.

3. The vascular access system of claim 1, wherein the housing comprises a stepped surface, wherein the cannula hub comprises a flange, wherein the flange contacts the stepped surface.

4. The vascular access system of claim 3, wherein the stepped surface forms the proximal opening of the housing.

* * * * *